(12) United States Patent
Park et al.

(10) Patent No.: US 11,359,224 B2
(45) Date of Patent: Jun. 14, 2022

(54) ENZYME-IMMOBILIZED POROUS MEMBRANE AND PREPARATION METHOD OF ANTIBIOTICS USING THE SAME

(71) Applicant: GWANGJU INSTITUTE OF SCIENCE AND TECHNOLOGY, Gwangju (KR)

(72) Inventors: Ji-woong Park, Gwangju (KR); Sunoh Shin, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 340 days.

(21) Appl. No.: 16/658,705

(22) Filed: Oct. 21, 2019

(65) Prior Publication Data
US 2020/0063175 A1 Feb. 27, 2020

Related U.S. Application Data

(62) Division of application No. 15/288,190, filed on Oct. 7, 2016, now abandoned.

(60) Provisional application No. 62/238,145, filed on Oct. 7, 2015.

(30) Foreign Application Priority Data

Jun. 2, 2016 (KR) .......................... 10-2016-0068897

(51) Int. Cl.
| | |
|---|---|
| C12P 37/04 | (2006.01) |
| C12N 9/84 | (2006.01) |
| C12N 11/093 | (2020.01) |

(52) U.S. Cl.
CPC ................ *C12P 37/04* (2013.01); *C12N 9/84* (2013.01); *C12N 11/093* (2020.01); *C12Y 305/01011* (2013.01)

(58) Field of Classification Search
CPC .......... C12P 37/04; C12N 11/093; C12N 9/84
See application file for complete search history.

(56) References Cited

U.S. PATENT DOCUMENTS

| | | | |
|---|---|---|---|
| 5,801,011 A | 9/1998 | Gardner | |
| 9,840,701 B2 | 12/2017 | Park et al. | |
| 10,202,596 B2 | 2/2019 | Park et al. | |
| 2015/0099288 A1* | 4/2015 | Park .................... | C12N 11/093 |
| | | | 435/182 |

FOREIGN PATENT DOCUMENTS

| | | | |
|---|---|---|---|
| JP | H08242884 | * | 9/1996 |
| KR | 10-0516271 B1 | | 9/2005 |

OTHER PUBLICATIONS

Ji-Woong Park et al, "Immobilization of enzyme into the nanoporous organic networks", The Polymer Society of Korea, published on Oct. 6, 2015, South Korea.

* cited by examiner

*Primary Examiner* — Ruth A Davis
(74) *Attorney, Agent, or Firm* — Novick, Kim & Lee, PLLC; Jae Youn Kim; Jihun Kim

(57) ABSTRACT

The present disclosure relates to an enzyme-immobilized porous membrane and a preparation method of antibiotics using the same, and more specifically, to an enzyme-immobilized porous membrane prepared by immobilizing a specific enzyme through dead-end filtration, and a preparation method of antibiotics with a high yield using the enzyme-immobilized porous membrane.

According to various exemplary embodiments of the present disclosure, the enzyme capable of promoting the synthesis reaction of the antibiotic substance is able to be stably immobilized in the porous membrane by passing the solution of enzyme through the membrane.

In addition, it is possible to provide antibiotics with a high yield by preparing the antibiotics by passing the reactant solution through the enzyme-immobilized porous membrane.

3 Claims, 6 Drawing Sheets

ENZYME-IMMOBILIZED POROUS MEMBRANE AND PREPARATION METHOD OF ANTIBIOTICS USING THE SAME

CROSS REFERENCE TO RELATED APPLICATION

This application is a Divisional application to U.S. patent application Ser. No. 15/288,190, filed on Oct. 7, 2016, which claims the priority of U.S. Provisional Application No. 62/238,145, filed on Oct. 7, 2015, and Korean Patent Application No. 10-2016-0068897, filed on Jun. 2, 2016 in the KIPO (Korean Intellectual Property Office), all of which are incorporated herein by reference in their entireties.

BACKGROUND

1. Technical Field

The present disclosure relates to an enzyme-immobilized porous membrane and a preparation method of antibiotics using the same, and more specifically, to an enzyme-immobilized porous membrane prepared by immobilizing a specific enzyme through filtration, and a preparation method of antibiotics with a high yield using the enzyme-immobilized porous membrane.

2. Description of the Related Art

Enzymes are generally useful for various reactions due to high steric and chemical selectivity, and have been used as a catalyst to promote a reaction rate under a mild reaction condition. However, in general, since the enzymes have a high cost, it is economically difficult to be used in an industrially large amount. In addition, most of the enzymes have a limitation in being used for an organic chemical reaction since they are not dissolved in organic solvents. Accordingly, a number of researches to immobilize the enzymes have been conducted to enhance activity and stability of the enzymes and reuse the enzymes.

There are three methods to immobilize the enzyme in a polymer membrane. The first method is to adsorb the enzyme on a surface of the polymer membrane, the second method is to attach the enzyme to the polymer membrane via a covalent bond by modifying the enzyme, and the third method is an entrapping method in which the enzyme is physically entrapped in pores of the polymer membrane.

Since the method of adsorbing the enzyme on the surface of the membrane via a non-covalent bond is the easiest and simplest, a number of researches into the adsorption method have been conducted, but the adsorption method is disadvantageous in that the enzyme may be easily leached away, and has relatively low stability.

In order to solve these disadvantages, there is an attempt to immobilize the enzyme in a porous membrane, and the immobilization method is effective to improve an immobilization rate and an immobilization maintenance rate of the enzyme and is effective in view of economical aspect since the immobilization process is relatively simple.

Penicillin-based antibiotics are β-lactam-based antibiotics produced by blue mold (*Penicillium notatum*), etc., and may be synthesized from *Penicillium notatum* and *Penicillium chrysogenum* that are called the blue mold.

In the related art, the antibiotics are synthesized by treating a derivative in a solution state through step-by-step reactions. However, this preparation method causes side reactions such as hydrolysis reaction and thus the final antibiotic substance is produced in a remarkably low yield.

Therefore, according to the present disclosure, the enzyme-immobilized porous membrane is used to stably immobilize the enzyme capable of promoting reactivity of the antibiotic substance in the porous membrane, thereby improving the reactivity, such that the antibiotic that is a final substance may have an improved yield.

SUMMARY

It is an aspect of the present disclosure to provide a porous membrane in which an enzyme capable of promoting a synthesis reaction of an antibiotic substance is stably immobilized by using dead-end filtration.

In addition, it is another aspect of the present disclosure to provide a preparation method of antibiotics with a high yield by using the enzyme-immobilized porous membrane.

The present disclosure is not limited to the above aspect and other aspects of the present disclosure will be clearly understood by those skilled in the art from the following description.

In accordance with one aspect of the present disclosure, there is provided an enzyme-immobilized porous membrane in which an enzyme promoting a synthesis reaction of an antibiotic substance is immobilized, wherein the porous membrane is three-dimensionally interconnected by pores, the porous membrane forms a three dimensional network by polymerizing a first monomer and a second monomer each having two to four functional groups, the functional group of the first monomer is an amino group, the functional group of the second monomer is an isocyanate group, an acyl halide group or an ester group, the first monomer and/or the second monomer has four functional groups, and the enzyme is at least one selected from the group consisting of penicillin G acylase, penicillin V acylase, and cephalosporin C acylase.

In accordance with another aspect of the present disclosure, a preparation method of antibiotics includes: (B) permeating a derivative solution of an antibiotic substance through the enzyme-immobilized porous membrane as described above.

According to various exemplary embodiments of the present disclosure, the enzyme capable of promoting the synthesis reaction of the antibiotic substance is able to be stably immobilized in the porous membrane by using the dead-end filtration.

Further, it is possible to provide the antibiotics with a high yield by preparing the antibiotics through the dead-end filtration using the enzyme-immobilized porous membrane.

DETAILED DESCRIPTION

Figure 1:
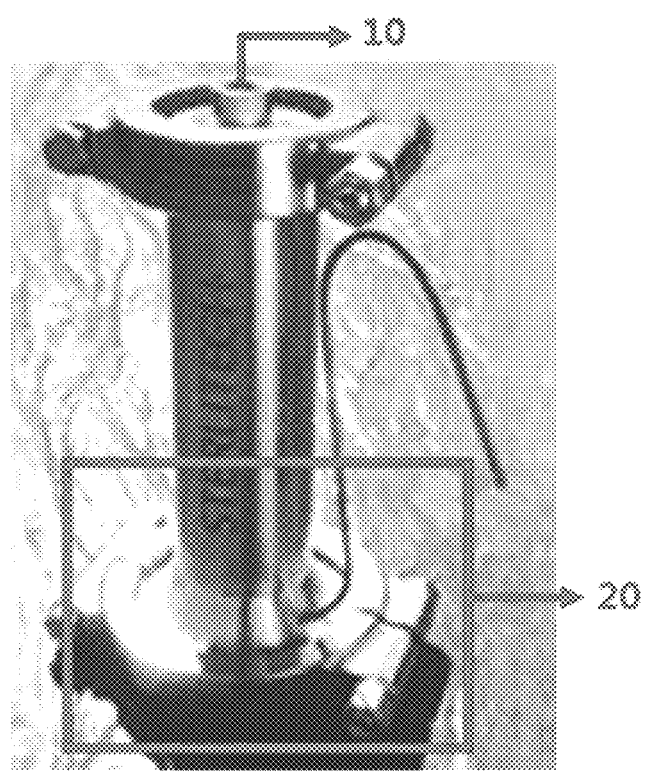
FIG. 1 illustrates a dead-end cell filtration system for immobilizing an enzyme according to an exemplary embodiment of the present disclosure.
Figure 2:
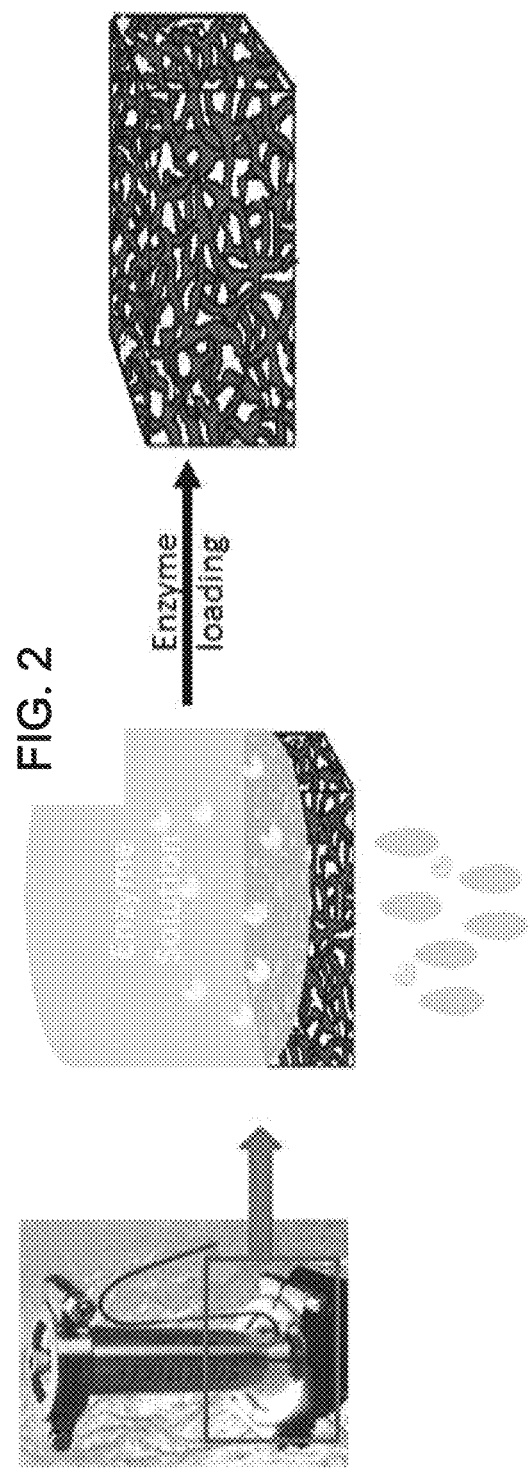
FIG. 2 is a diagram illustrating a preparation method in which the enzyme is immobilized in the porous membrane according to the exemplary embodiment of the present disclosure.

Hereinafter, various aspects and exemplary embodiments of the present disclosure will be described in detail.

According to one aspect of the present disclosure, there is provided an enzyme-immobilized porous membrane in which an enzyme promoting a synthesis reaction of an antibiotic substance is immobilized, wherein the porous membrane is three-dimensionally interconnected by pores, the porous membrane forms a three-dimensional network by polymerizing a first monomer and a second monomer each having two to four functional groups, the functional group of the first monomer is an amino group, the functional group of the second monomer is an isocyanate group, an acyl halide group or an ester group, at least one of the first monomer or the second monomer has four functional groups, and the enzyme is at least one selected from the group consisting of penicillin G acylase, penicillin V acylase, and cephalosporin C acylase.

The enzymes are characterized by promoting a synthesis reaction of an antibiotic substance, and among them, the penicillin G acylase is an enzyme capable of promoting reactions of Reaction Schemes 1 and 2 below:

[Reaction Scheme 1]

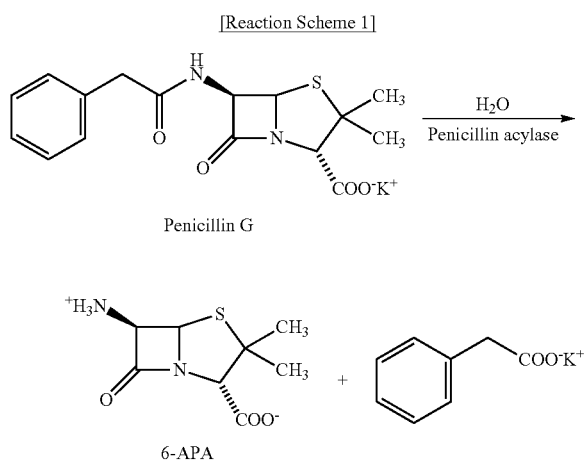

Firstly, as shown in Reaction Scheme 1 above, carboxylic acid and 6-aminopenicillanic acid (6-APA) may be produced by promoting a hydrolysis reaction of an amide group.

Secondly, as shown in Reaction Scheme 2 below, a reaction of synthesizing penicillin-based amoxicillin which is a beta-lactam-based antibiotic may be promoted, and specifically, the penicillin may be synthesized by promoting a reaction of an ester group of p-hydroxyphenylglycine methyl ester (PHPGME) and an amine group of 6-APA to form an amide group:

[Reaction Scheme 2]

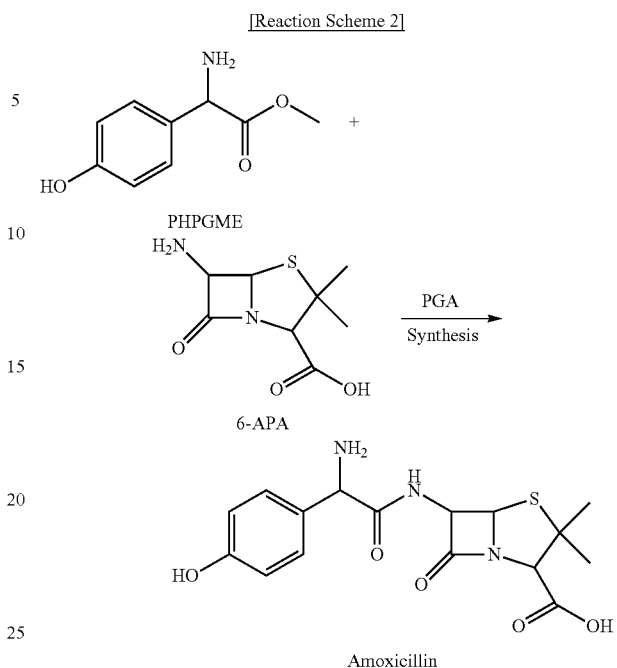

The penicillin G acylase enzyme may act as a catalyst effective for promoting reactivity in synthesizing the penicillin-based antibiotic, but has a problem in that stability thereof is degraded due to the hydrolysis as shown in Reaction Scheme 1 above.

Accordingly, in the present disclosure, the enzyme is immobilized in the porous membrane to prevent decomposition or leaching of the enzyme, such that stability of the enzyme may be secured.

In addition, antibiotics with a high yield may be prepared only by a relatively simple process in which a derivative of the antibiotic substance is permeated through the porous membrane in which the enzyme having secured stability is immobilized.

Specifically, the enzyme-immobilized porous membrane described above in the present disclosure includes the porous membrane forming a three-dimensional network and an enzyme that is trapped in the pores of the porous membrane. The porous membrane may include the pores having a size of 5 to 100 nm while forming a three-dimensionally cross-linked monolith, and the pores may be connected to each other, such that the enzyme immobilized in the porous membrane is able to be in contact with reaction substrates in all directions, and a solution may be easily spread, which prevent a problem that substance transport is degraded due to the enzyme blocking the pores.

In addition, in order for the enzyme to be immobilized in the porous membrane, it is generally known that the size of the pore is 20 to 50 nm (Membrane-Based Synthesis of Nanomaterials, Charles R. Martin), and the porous membrane of the present disclosure is characterized by immobilizing various sizes of enzymes since it has various ranges of nano pores having a size of 5 to 100 nm as well as pores having a size in micro range.

The porous membrane of the present disclosure may be obtained by mixing an organic sol with a polymer solution to obtain a micro porous membrane, the organic sol consisting of an organic network structure in which the first monomer having an amino group is polymerized with the second monomer having an isocyanate group, an acyl halide group or an ester group that is the functional group polymerizable with the amino group, and removing the polymer from the micro porous membrane by using water.

According to an exemplary embodiment of the present disclosure, the first monomer may have two to four amino groups, and the second monomer may have two to four functional groups selected from the group consisting of the isocyanate group, the acyl halide group, and the ester group. The first monomer having two to four amino groups may be $C_1$-$C_{100}$ aliphatic compound substituted with two to four amino groups or $C_6$-$C_{100}$ aromatic compound substituted with two to four amino groups.

The second monomer having two to four isocyanate groups, the two to four acyl halide groups, or the two to four ester groups may be $C_1$-$C_{100}$ aliphatic compound substituted with two to four isocyanate groups, the two to four acyl halide groups, or the two to four ester groups or $C_6$-$C_{100}$ aromatic compound substituted with two to four isocyanate groups, the two to four acyl halide groups, or the two to four ester groups.

As an example, the first monomer and the second monomer may be compounds represented by Chemical Formulas 1 to 9 below:

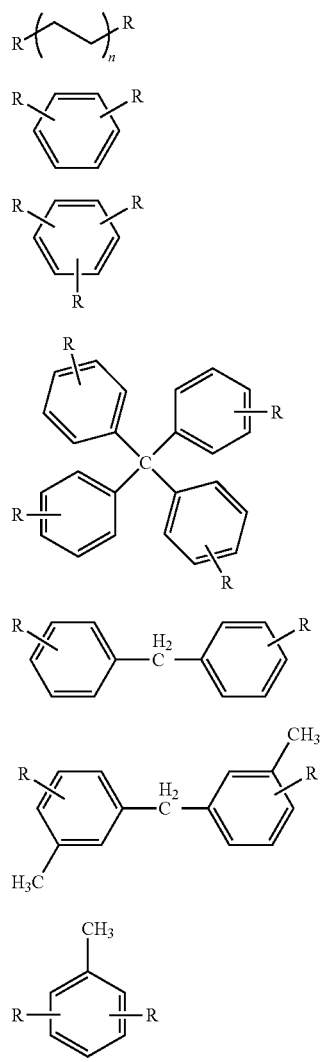

[Chemical Formula 1]

[Chemical Formula 2]

[Chemical Formula 3]

[Chemical Formula 4]

[Chemical Formula 5]

[Chemical Formula 6]

[Chemical Formula 7]

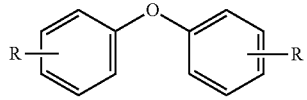

[Chemical Formula 8]

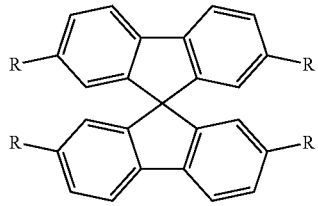

[Chemical Formula 9]

in Chemical Formulas 1 to 9 above, R is an amino group, an isocyanate group, an acyl halide group or an ester group.

In addition, according to an exemplary embodiment of the present disclosure, the first monomer and the second monomer may be a compound represented by Chemical Formula 10 below:

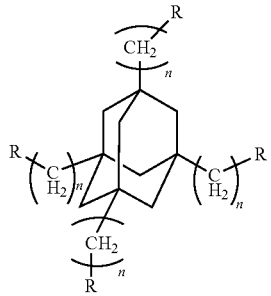

[Chemical Formula 10]

in Chemical Formula 10 above, R is an amino group, an isocyanate group, an acyl halide group or an ester group, and n is 0 or 1.

The first monomer and the second monomer may be polymerized by a nucleophilic addition or substitution reaction between the amino group of the first monomer and the isocyanate group, the acyl halide group or the ester group of the second monomer, and polymers to be produced may cause additional nucleophilic addition or substitution reaction by non reacted negative (−), positive (+) functional groups to generate a crosslinking reaction between the polymers. As a result, the monomer having the four functional groups may form a kind of crosslinking point as a tetrahedral structure, and may form the three-dimensional organic network structure linked by a strong covalent bond on the basis of the crosslinking point.

Specifically, the organic network structure formed by the polymerization reaction between the first monomer and the second monomer may be three-dimensionally polymerized and cross-linked to have a number of fine pores and a large specific surface area, and to have excellent chemical resistance, heat resistance, and durability by a high crosslinking rate and the strong covalent bond.

In addition, the monomer having two to four amino groups may be, for example, tetrakis(4-aminophenyl)methane (TAPM), p-phenylene diamine (PDA), or 4,4'-oxydianiline (ODA), but these examples thereof are not limited thereto.

Further, the monomer having two to four isocyanate groups may be, for example, p-phenylene diisocyanate (PDI), hexamethylene diisocyanate (HDI), or tetrakis(4-isocyanatophenyl)methane (TIPM), but these examples thereof are not limited thereto.

According to an exemplary embodiment of the present disclosure, the porous membrane may be formed by polymerizing a monomer represented by Chemical Formula 11 below and the monomer having two isocyanate groups:

[Chemical Formula 11]

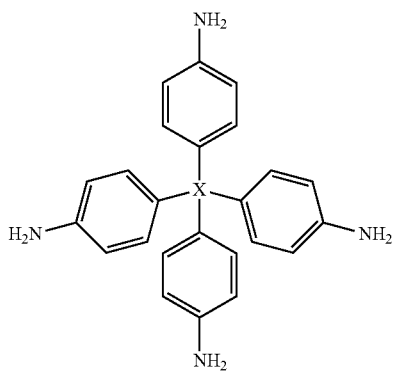

in Chemical Formula 11 above, X is a carbon atom or a silicon atom.

Further, according to another exemplary embodiment of the present disclosure, the porous membrane may be formed by polymerizing the monomer having two amino groups and a monomer represented by Chemical Formula 12 below:

[Chemical Formula 12]

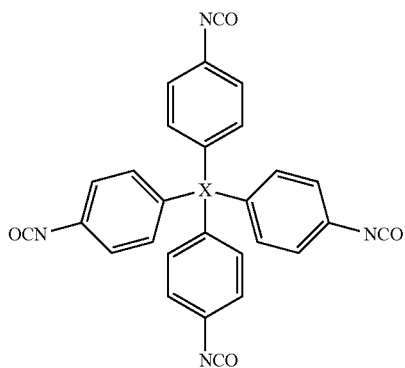

in Chemical Formula 12 above, X is a carbon atom or a silicon atom.

The porous membrane may have a flat sheet structure or a hollow fiber membrane structure.

In addition, the porous membrane may have a single layered structure or a plurality of layered structure.

According to another aspect of the present disclosure, there is provided a preparation method of antibiotics including: (B) permeating a derivative solution of an antibiotic substance through the enzyme-immobilized porous membrane.

The preparation method preferably further includes step (A) of preparing the derivative solution of the antibiotic substance.

According to the related art, the derivative of the antibiotic substance is prepared in a solution state, and is treated with step-by-step reactions, thereby preparing the antibiotics. The preparation method of the antibiotics through the step-by-step reactions has problems in that the finally produced antibiotic substance has a remarkably low yield, and a large amount of impurities are caused due to the hydrolysis reaction or the addition reaction of the enzyme.

Accordingly, according to the present disclosure, stability of the enzyme is firstly secured by immobilizing the enzyme in the porous membrane, and then, the antibiotics with a high yield are prepared only by a simple process of permeating the derivative of the antibiotic substance through the enzyme-immobilized porous membrane.

Specifically, step (A) is a step of preparing the derivative solution of the antibiotic substance capable of preparing the antibiotic substance.

The derivative of the antibiotic substance preferably includes the first derivative and the second derivative, and the first derivative and the second derivative may be different from each other, and the first derivative or the second derivative may be at least one selected from the group consisting of 6-aminopenicillanic acid (6-APA), p-hydroxyphenylglycine methyl ester (PHPGME), 7-aminodesacetoxycephalosporanic acid, and phenylglycine.

The step (A) may include (a-1) preparing a first derivative solution; (a-2) preparing a second derivative solution; and (a-3) mixing the first derivative solution with the second derivative solution.

The step (a-1) is a step of preparing the first derivative solution, wherein the first derivative solution preferably has a concentration of 1 to 20 mM by adding a solvent to the first derivative. When the concentration of the first derivative solution is less than 1 mM, it is not preferred since the concentration is too thin, reactivity with the enzyme may be degraded, and when the concentration thereof is more than 20 mM, an amount of the reaction substance is increased as compared to an amount of the enzyme.

The step (a-2) is a step of preparing the second derivative solution, wherein the second derivative solution preferably has a concentration of 1 to 20 mM by adding a solvent to the second derivative, which is similar to the step (a-1).

The solvent is preferably distilled water, but the present disclosure is not limited thereto.

The step (a-3) is a step of mixing the first derivative solution with the second derivative solution, wherein the first derivative and the second derivative are preferably mixed at a molar (M) ratio of 1:1 to 3. When the molar ratio is out of the above-described range, it is not preferred since reactivity may be degraded.

In particular, it is confirmed that when the first derivative is 6-aminopenicillanic acid, the second derivative is p-hydroxyphenylglycine methyl ester, and the 6-aminopenicillanic acid is mixed with the p-hydroxyphenylglycine methyl ester at a molar (M) ratio of 1:2, a penicillin-based antibiotic to be synthesized has the most effective yield as about 70%, and when the molar ratio is out of the above-described range, the yield is rapidly reduced.

The step (B) is a step of permeating the derivative solution of the antibiotic substance through the enzyme-immobilized porous membrane.

Here, the derivative solution of the antibiotic substance to be added preferably has a content of 0.8 to 10 parts by weight relative to 100 parts by weight of the porous membrane.

The permeating step is preferably performed by applying a pressure of 1 to 10 bar in a nitrogen atmosphere through dead-end filtration, cross flow filtration, or a complex manner thereof.

In particular, it is confirmed that when 1 to 5 parts by weight of the derivative solution of the antibiotic substance is permeated through the dead-end filtration at a pressure of 5 bar in a nitrogen atmosphere, the amount of impurities contained in the antibiotic which is the final product is rapidly reduced.

Hereinafter, the present disclosure will be described in detail with reference to the following Examples, etc. Therefore, it should be understood that the foregoing embodiments are provided for illustrative purposes only and are not to be construed in any way as limiting the present disclosure. In addition, as long as a person skilled in the art practices the present disclosure based on the disclosed description of the present disclosure including the following examples, it is obvious that the present disclosure may be easily practiced by the person skilled in the art even though testing results are not specifically provided, and it is natural that various modifications and changes are included in the accompanying claims.

In addition, experimental results below are only representative experimental results of Examples and Comparative Examples of the present disclosure, and respective effects of various embodiments of the present disclosure that are not presented explicitly below are described in detail in corresponding sections.

Preparation Example: Preparation of Porous Membrane (1) Preparation of (TAPM+HDI/PEG) Nano Composite Film Tetrakis(4-aminophenyl) methane (TAPM) (MW: 382.50) was dissolved in DMF (N,N-dimethylformide) to prepare an organic solution having a concentration of 4 wt/vol %, and 1,4-hexamethylene diisocyanate (HDI) (MW: 168.19) was dissolved in DMF to prepare an organic solution having a concentration of 4 wt/vol %. Next, the tetrakis(4-aminophenyl) methane solution was slowly added to the 1,4-hexamethylene diisocyanate solution, and mixed with each other. The mixed solution was reacted at room temperature in a nitrogen atmosphere for 72 hours, to obtain a mixed solution in a sol-phase.

Poly ethylene glycol (PEG) having a concentration of 60 wt % was added to the mixed solvent, followed by sufficient stirring. The obtained mixture was applied to a glass plate at 50° C. for 1 hour, at 80° C. for 2 hours, and at 100° C. for 3 hours, followed by drying and curing, to finally synthesize a nano composite film of an organic molecular network (TAPM+HDI) and PEG.

(2) Preparation of TAPM+HDI Porous Membrane—Removal of PEG

The synthesized membrane was cooled at room temperature, and precipitated in water to be separated from a substrate. The membrane was stirred in water for about one week to remove the water-soluble polymer, polyethylene glycol (PEG), thereby preparing a porous membrane having nano pores.

Example 1: Preparation of PGA-Immobilized Porous Membrane

The porous membrane of Preparation Example for immobilizing the enzyme was put into a lower portion 20 of a dead-end cell filtration system as illustrated in FIG. 1. Then, a penicillin G acylase (PGA) solution having a concentration of 0.4 w/v % was put into an upper portion (inlet, 10) of the dead-end cell filtration system, and stirred. Next, a pressure of 5 bar was applied in a nitrogen atmosphere to prepare a porous membrane in which the penicillin G acylase (PGA) is immobilized.

Example 2: Preparation of Antibiotic

First, the PGA-immobilized porous membrane prepared by Example 1 above was put into the lower portion 20 of the dead-end cell filtration system.

Then, 10 mM p-hydroxyphenylglycine methyl ester (PHPGME) solution and 10 mM 6-aminopenicillanic acid (6-APA) solution were prepared, respectively, by using distilled water as a solvent, and two of the prepared solutions were mixed and put into the upper portion (inlet, 10) of the dead-end cell filtration system. Next, a pressure of 5 bar was applied in a nitrogen atmosphere to permeate the mixed solution of PHPGME and 6-APA through the PGA-immobilized porous membrane, thereby preparing an antibiotic.

(Provided that, the dead-end cell filtration system was used as the same as that of Example 1 above.)

Test Example 1: Analysis of Pores of Porous Membrane

In order to confirm a pore size of the PGA-immobilized porous membrane according to Example 1, nitrogen was added and adsorbed onto or desorbed from the porous membrane. Results thereof were illustrated in FIG. 3.

Figure 3:
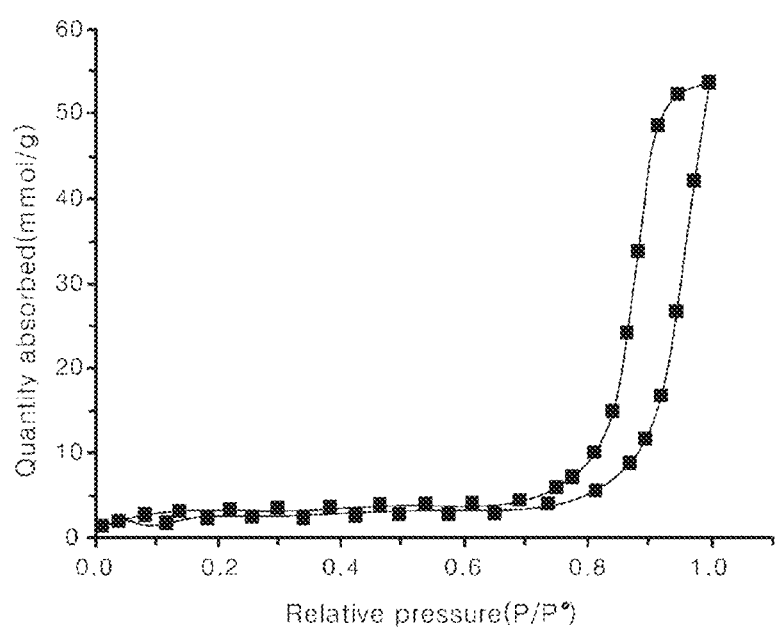
FIG. 3 is a graph illustrating results obtained by adsorbing nitrogen onto or desorbing nitrogen from a PGA-immobilized porous membrane according to Example 1 to measure an adsorption degree or a desorption degree.
Figure 4:
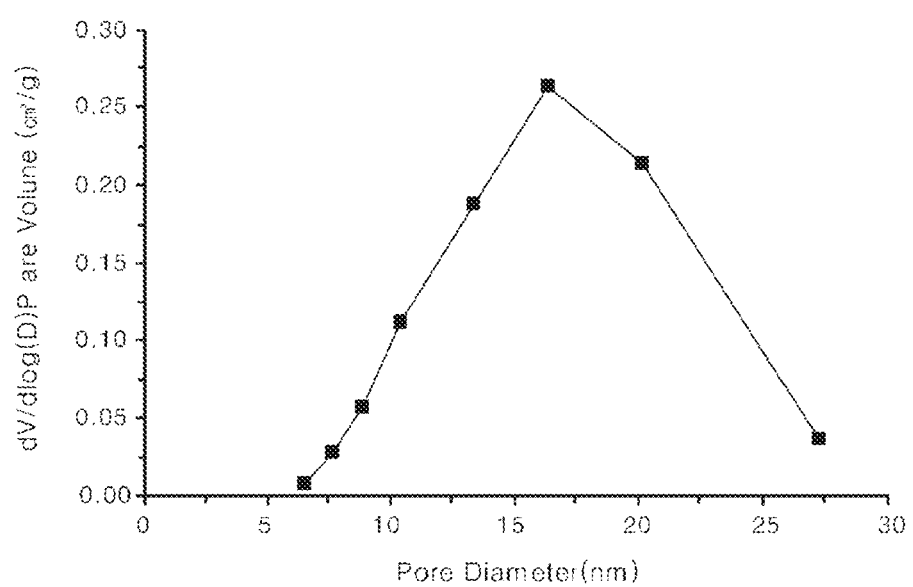
FIG. 4 is a graph illustrating results obtained by measuring a size of pores formed on the PGA-immobilized porous membrane according to Example 1.

Referring to FIG. 3, it could be appreciated that an adsorption and desorption curve of Type 4 isotherm was obtained, and the pores were well-formed in the porous membrane. The size of the thus formed pores was measured, and illustrated in FIG. 4. Referring to FIG. 4, it could be confirmed that the pore size of the porous membrane had an average diameter of 5 to 30 nm.

Test Example 2: Analysis to Whether Enzyme is Immobilized in Porous Membrane

Figure 5A:
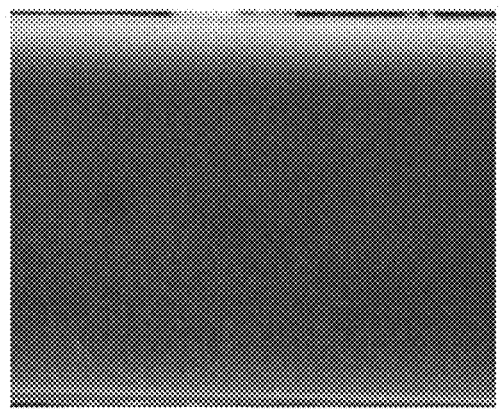
FIG. 5A is an image illustrating a cross section of the PGA-immobilized porous membrane according to Example 1.
Figure 5B:
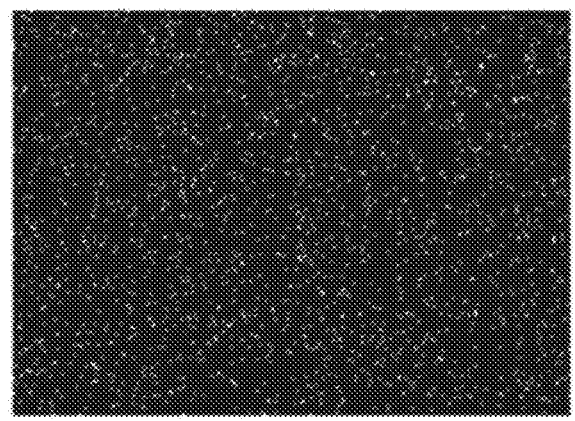
FIG. 5B is an image illustrating results obtained by elemental mapping on the PGA-immobilized porous membrane according to Example 1 using an energy-dispersive X-ray spectrometer.

In order to confirm whether the enzyme was well immobilized in the PGA-immobilized porous membrane of Example 1, elemental mapping was performed by using an energy-dispersive X-ray spectrometer (JOEL JSM-6700 manufactured by Scanning Electron Microscope), and results thereof were illustrated in FIG. 5A and FIG. 5B.

FIG. 5A is an image illustrating a cross section of the porous membrane according to Example 1.

The porous membrane is composed of carbon, nitrogen, and oxygen, and the enzyme is composed of carbon, nitrogen, oxygen and sulfur, and thus, whether the enzyme is immobilized could be confirmed by analyzing whether the sulfur element is present.

Accordingly, as a result obtained by performing the elemental mapping with regard to the sulfur element, it could be appreciated that the sulfur elements represented by white dots were uniformly distributed as illustrated in FIG. 5B. Specifically, it could be confirmed that the enzyme was uniformly distributed in the inside of the cross section of the porous membrane.

Test Example 3: Quantitative Analysis of Antibiotic

In order to quantitatively analyze the antibiotic prepared by Example 2, the antibiotic substance was separated by using a Phenomenex Gemini C18 column (150×4.6 mm, a particle size of 5 μm) through a high performance liquid chromatography (HPLC), and was subjected to quantitative analysis by measuring an adsorption amount of the antibiotic with an UV detector at 225 nm. The conversion amount was calculated by the following Calculation Formula 1, and results thereof were illustrated in FIG. 6.

Conversion (%)=(experimental amoxicillin amount/theoretical amoxicillin amount)×100   [Calculation Formula 1]

Figure 6:
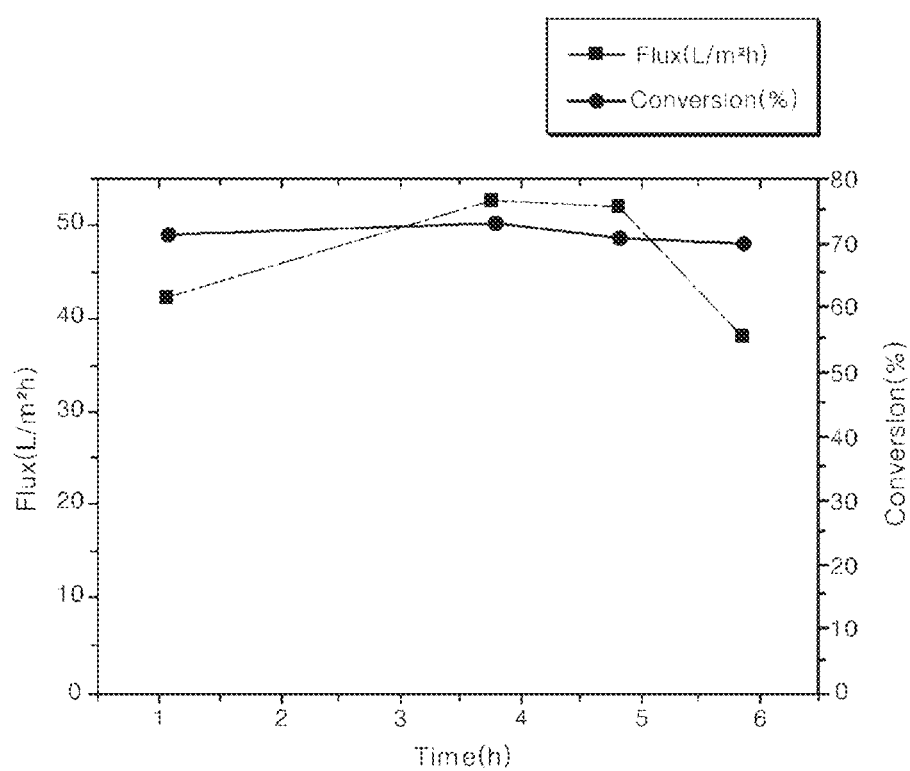
FIG. 6 is a graph illustrating results obtained by measuring a yield of the antibiotic prepared by Example 2.

Referring to FIG. 6, it could be confirmed that about 70% constant conversion was obtained. The result value was significantly improved as compared to a yield obtained by the existing preparation method of antibiotics, and reactivity was improved due to the reaction in which the enzyme immobilized in the porous membrane was promoted, which indicated that the antibiotics with a high yield could be prepared.

Therefore, according to various exemplary embodiments of the present disclosure, the enzyme capable of promoting the synthesis reaction of the antibiotic substance is able to be stably immobilized in the porous membrane by using the dead-end filtration.

Further, it is possible to provide the antibiotics with a high yield by preparing the antibiotics through the dead-end filtration using the enzyme-immobilized porous membrane.

Although some embodiments have been disclosed herein, it should be understood by those skilled in the art that these embodiments are provided by way of illustration only, and that various modifications, changes, and alterations can be made without departing from the spirit and scope of the invention. Therefore, it should be understood that the foregoing embodiments are provided for illustrative purposes only and are not to be construed in any way as limiting the present disclosure.

What is claimed is:

1. A preparation method of antibiotics comprising:
(A) preparing a derivative solution of an antibiotic substance; and
(B) permeating the derivative solution of the antibiotic substance through an enzyme-immobilized porous membrane,
wherein the enzyme-immobilized porous membrane is immobilized with an enzyme promoting a synthesis reaction of the antibiotic substance and is three-dimensionally interconnected by pores, the enzyme-immobilized porous membrane forming a three-dimensional network by polymerizing a first monomer and a second monomer,
wherein the step (A) includes:
(a-1) preparing a first derivative solution;
(a-2) preparing a second derivative solution; and
(a-3) mixing the first derivative solution with the second derivative solution,
wherein the first derivative solution includes 6-aminopenicillanic acid and the second derivative solution includes p-hydroxyphenylglycine methyl ester,
wherein the first monomer is tetrakis(4-aminophenyl)methane (TAPM), p-phenylene diamine (PDA), or 4,4'-oxydianiline (ODA), and the second monomer is p-phenylene diisocyanate (PDI), hexamethylene diisocyanate (HDI), or tetrakis(4-isocyanatophenyl)methane (TIPM),
wherein the enzyme is at least one selected from a group consisting of penicillin G acylase, penicillin V acylase, and cephalosporin C acylase, and
wherein the step (B) is performed at a pressure of 2 to 7 bar in a nitrogen atmosphere.

2. The preparation method according to claim 1, wherein the first derivative solution and the second derivative solution are mixed at a molar (M) ratio of 1:1 to 3.

3. The preparation method according to claim 1, wherein the permeating of the step (B) is performed by dead-end filtration.

* * * * *